United States Patent
Gale et al.

(10) Patent No.: US 7,011,844 B2
(45) Date of Patent: Mar. 14, 2006

(54) FORMULATIONS FOR THE ADMINISTRATION OF FLUOXETINE

(75) Inventors: Robert M. Gale, Los Altos, CA (US); Melinda K. Nelson, Sunnyvale, CA (US); Michel J. N. Cormier, Mountain View, CA (US); Suneel K. Gupta, Sunnyvale, CA (US); Patricia S. Campbell, Palo Alto, CA (US)

(73) Assignee: Alza Corporation, Mountain View, CA (US)

( * ) Notice: Subject to any disclaimer, the term of this patent is extended or adjusted under 35 U.S.C. 154(b) by 195 days.

(21) Appl. No.: 10/302,490

(22) Filed: Nov. 22, 2002

(65) Prior Publication Data

US 2003/0166624 A1 Sep. 4, 2003

Related U.S. Application Data

(63) Continuation of application No. 08/892,118, filed on Jul. 14, 1997, now Pat. No. 6,512,010.
(60) Provisional application No. 60/038,425, filed on Feb. 19, 1997, and provisional application No. 60/021,727, filed on Jul. 15, 1996.

(51) Int. Cl.
*A61K 9/70* (2006.01)

(52) U.S. Cl. .................. 424/449; 424/443; 424/447; 514/649

(58) Field of Classification Search .............. 424/435, 424/445, 447, 449; 514/649
See application file for complete search history.

(56) References Cited

U.S. PATENT DOCUMENTS

| 429,356 A | 5/1890 | Holland ................ 424/274 |
| 3,598,122 A | 8/1971 | Zaffaroni ................ 128/268 |
| 3,598,123 A | 8/1971 | Zaffaroni ................ 128/268 |
| 3,731,683 A | 5/1973 | Zaffaroni ................ 128/268 |
| 3,797,494 A | 3/1974 | Zaffaroni ................ 128/268 |
| 4,031,894 A | 6/1977 | Urquhart et al. .......... 128/268 |

(Continued)

FOREIGN PATENT DOCUMENTS

| DE | 43 01 783 C1 | 2/1994 |
| WO | WO 92/18005 | 10/1992 |
| WO | WO92/19226 | 11/1992 |
| WO | WO94/21262 | 9/1994 |
| WO | WO 95/01167 | 1/1995 |
| WO | WO 95/09006 | 4/1995 |
| WO | WO 95/28151 | 10/1995 |
| WO | WO 96/37231 | 11/1996 |
| WO | WO 96/40259 | 12/1996 |
| WO | WO97/10816 | 3/1997 |

OTHER PUBLICATIONS

Knepp, Victoria M., et al., Transdermal Drug Delivery: Problems and Poasibilities, CRC Critical Reviews in Therapeutic Drug Carrier Systems, vol. 4, Issue 1 (1987), pp. 13–37.
Cleary, Gary W., Topical Drug Bioavailability: Bioequivalence, and Penetration, (1993), Transdermal Delivery Systems: A Medical Rationale, pp. 17–68.

*Primary Examiner*—Gary Kunz
*Assistant Examiner*—Konata M. George (57) ABSTRACT

Composition of matter for application to a body surface or membrane to administer fluoxetine by permeation through the body surface or membrane, the composition comprising fluoxetine to be administered, at a therapeutically effective rate, alone or in combination with a permeation enhancer or mixture. A preferred embodiment is directed to the transdermal administration of fluoxetine at reduced skin irritation levels wherein fluoxetine, preferably provided as fluoxetine acetate, is coadministered with a corticosteroid such as hydrocortisone. Also disclosed are drug delivery devices containing the fluoxetine or fluoxetine and enhancer composition and methods for the transdermal administration of the fluoxetine and fluoxetine/enhancer composition.

10 Claims, 6 Drawing Sheets

U.S. PATENT DOCUMENTS

| | | | |
|---|---|---|---|
| 4,035,511 A | 7/1977 | Messing et al. | 424/330 |
| 4,083,982 A | 4/1978 | Messing et al. | 424/260 |
| 4,144,317 A | 3/1979 | Higuchi et al. | 424/21 |
| 4,201,211 A | 5/1980 | Chandrasekaran | 128/268 |
| 4,286,592 A | 9/1981 | Chandrasekaran | 128/260 |
| 4,314,081 A | 2/1982 | Molloy et al. | 564/347 |
| 4,314,557 A | 2/1982 | Chandrasekaran | 128/260 |
| 4,329,356 A | 5/1982 | Holland | 424/274 |
| 4,379,454 A | 4/1983 | Campbell et al. | 604/897 |
| 4,435,180 A | 3/1984 | Leeper | 604/896 |
| 4,444,778 A | 4/1984 | Coughlin | 424/262 |
| 4,552,872 A | 11/1985 | Cooper et al. | 514/175 |
| 4,559,222 A | 12/1985 | Enscore et al. | 424/28 |
| 4,568,343 A | 2/1986 | Leeper et al. | 604/896 |
| 4,573,995 A | 3/1986 | Chen et al. | 604/896 |
| 4,588,580 A | 5/1986 | Gale et al. | 424/21 |
| 4,590,213 A | 5/1986 | Stark | 514/653 |
| 4,594,358 A | 6/1986 | Hynes | 514/651 |
| 4,626,549 A | 12/1986 | Molloy et al. | 514/651 |
| 4,645,502 A | 2/1987 | Gale et al. | 604/896 |
| 4,647,591 A | 3/1987 | Cherkin et al. | 514/651 |
| 4,683,235 A | 7/1987 | Hynes | 514/282 |
| 4,704,282 A | 11/1987 | Campbell et al. | 424/449 |
| 4,746,515 A | 5/1988 | Cheng et al. | 424/449 |
| 4,756,710 A | 7/1988 | Bondi et al. | 424/449 |
| 4,788,062 A | 11/1988 | Gale et al. | 424/449 |
| 4,816,258 A | 3/1989 | Nedberge et al. | 424/448 |
| 4,849,226 A | 7/1989 | Gale | 424/448 |
| 4,863,738 A | 9/1989 | Taskovich | 424/449 |
| 4,865,848 A | 9/1989 | Cheng et al. | 424/449 |
| 4,888,354 A | 12/1989 | Chang et al. | 514/424 |
| 4,895,845 A | 1/1990 | Seed | 514/252 |
| 4,904,475 A | 2/1990 | Gale et al. | 424/449 |
| 4,908,027 A | 3/1990 | Enscore et al. | 604/890 |
| 4,938,759 A | 7/1990 | Enscore et al. | 604/896.1 |
| 4,940,585 A | 7/1990 | Hapworth et al. | 424/464 |
| 4,943,435 A | 7/1990 | Baker et al. | 424/448 |
| 4,999,382 A | 3/1991 | Wurtman et al. | 514/646 |
| 5,000,956 A | 3/1991 | Amkraut et al. | 424/434 |
| 5,004,610 A | 4/1991 | Osborne et al. | 424/448 |
| 5,028,431 A | 7/1991 | Franz et al. | 424/449 |
| 5,049,387 A | 9/1991 | Amkraut | 424/435 |
| 5,104,899 A | 4/1992 | Young et al. | 514/646 |
| 5,122,382 A | 6/1992 | Gale et al. | 424/449 |
| 5,141,750 A | 8/1992 | Lee et al. | 424/448 |
| 5,151,448 A | 9/1992 | Crenshaw et al. | 514/651 |
| 5,225,585 A | 7/1993 | Schwartz et al. | 558/275 |
| 5,314,694 A | 5/1994 | Gale et al. | 424/448 |
| 5,342,623 A | 8/1994 | Enscore et al. | 424/448 |
| 5,356,934 A | 10/1994 | Robertson et al. | 514/649 |
| 5,378,730 A | 1/1995 | Lee et al. | 514/535 |
| 5,411,738 A | 5/1995 | Hind | 424/445 |
| 5,446,070 A | 8/1995 | Mantelle | 514/772.6 |
| 5,451,407 A | 9/1995 | Cormier et al. | 424/448 |
| 5,589,511 A | 12/1996 | Young et al. | 514/646 |
| 5,589,512 A | 12/1996 | Norden | 514/651 |
| 5,601,839 A | 2/1997 | Quan et al. | 424/448 |
| 5,613,958 A | 3/1997 | Kochinke et al. | |
| 5,635,203 A | 6/1997 | Gale et al. | 424/448 |
| 5,641,504 A | 6/1997 | Lee et al. | 424/447 |
| 5,648,396 A | 7/1997 | Young et al. | |
| 5,708,035 A | 1/1998 | Young et al. | |
| 5,785,991 A | 7/1998 | Burkoth et al. | |
| 6,203,817 B1 | 3/2001 | Cormier et al. | |
| 6,299,900 B1 | 10/2001 | Leonard et al. | |
| 6,419,913 B1 | 7/2002 | Niemiec et al. | |
| 6,420,351 B1 | 7/2002 | Tsai et al. | |
| 6,512,010 B1 * | 1/2003 | Gale et al. | 514/649 |

* cited by examiner

FORMULATIONS FOR THE ADMINISTRATION OF FLUOXETINE

RELATED APPLICATIONS

This application is a continuation of Ser. No. 08/892,118 filed on Jul. 14,1997 now U.S. Pat. No. 6,512,010, which claimed benefit of U.S. Provisional Application No. 60/021, 727, filed on Jul. 15, 1996 and No. 60/038,425 filed Feb. 19, 1997. This application is also related to U.S. Pat. No. 6,203,817, which is a continuation in part of U.S. Pat. No. 6,512,010.

FIELD OF INVENTION

This invention relates to sustained release formulations for the safe and efficacious administration of fluoxetine for, among other things, the treatment of depression. More particularly, the invention relates to novel methods, compositions, and devices for transdermally administering fluoxetine to a subject through a body surface or membrane over a sustained time period. A preferred embodiment is directed to the transdermal administration of fluoxetine at reduced skin irritation levels.

BACKGROUND OF THE INVENTION

Fluoxetine, (±)-N-methyl-γ-[4-(trifluoromethyl)-phenoxy] benzenepropanamine, is one of the 3-aryloxy-3-phenylpropylamine compounds described in U.S. Pat. No. 4,314,081. Additionally, U.S. Pat. No. 4,626,549 discloses a method of blocking the uptake of monoamines such as serotonin by brain neurons in animals comprising administering a "monoamine blocking amount" of a 3-aryloxy-3-phenylpropylamine compound, such as fluoxetine. It is a potent, highly selective reuptake inhibitor of serotonin (5-hydroxytryptamine) and is indicated for the treatment of depression and obsessions and compulsions related to obsessive-compulsive disorder (OCD). As an antidepressant or for the treatment of OCD, fluoxetine is administered orally as a solution or in tablets as fluoxetine hydrochloride (Prozac®) in 10 mg or 20 mg daily doses and has an elimination half-life of from 1–9 days, averaging about 2–3 days. Other methods for the production of fluoxetine and new intermediates are disclosed in U.S. Pat. No. 5,225,585. All of the above mentioned patents are hereby incorporated in their entirety by reference.

Fluoxetine is a racemic mixture (50/50) of R-fluoxetine and S-fluoxetine enantiomers. The delivery of the S(+) enantiomer is disclosed in the prior art. For example, U.S. Pat. No. 5,104,899 discloses a method of treating depression in a human patient comprising administering the S(+) enantiomer of fluoxetine in substantially optically pure form. PCT application WO 95/28152 discloses methods for treating or improving memory, and for treating sexual dysfunction, while avoiding the unwanted adverse toxic or psychological effects associated with the racemic mixture of fluoxetine, comprising administering a therapeutically effective amount of S(+) fluoxetine or a pharmaceutically acceptable salt thereof, substantially free of its R(−) stereoisomer.

The use of fluoxetine for indications other than treating depression is also disclosed in the following: U.S. Pat. Nos. 4,594,358, 4,647,591, 4,683,235, 4,940,585, 4,999,382, 5,151,448, 5,356,934, 5,446,070, 5,589,511, and PCT Application WO 92/18005. Transdermal delivery as a route of administering fluoxetine is mentioned in these patents, though specific formulations or delivery regimens are nowhere disclosed. Other uses of fluoxetine are disclosed in U.S. Pat. Nos. 4,035,511, 4,083,982, 4,329,356, 4,444,778, 4,590,213, 4,895,845, and 5,589,512, all of which do not disclose the transdermal administration route.

Additionally, U.S. Pat. No. 5,601,839 discloses transdermal formulations for enhancing dermal penetration of a basic drug, including fluoxetine, comprising a matrix formulation comprising an amount of the basic drug and a permeation enhancer consisting essentially of triacetin in a polymer layer, preferably a pressure sensitive adhesive.

The oral administration of fluoxetine in the treatment of depression is initiated with a 20 mg/day dose administered in the morning. If no improvement is observed over several weeks, the dosage may be increased, though not to exceed 80 mg/day. Doses above 20 mg/day should be administered once a day in the morning or by a b.i.d. schedule (morning and noon).

The transdermal route of parenteral delivery of drugs and other biologically active agents ("agents") has been proposed for a wide variety of systemically acting and locally acting agents on either a rate-controlled or non-rate-controlled basis and is described in numerous technical publications such as the following: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,573,995; 4,588,580; 4,645,502; 4,704,282; 4,788,062; 4,816,258; 4,849,226; 4,904,475; 4,908,027; 4,938,759; 4,943,435; 5,004,610; 5,122,382; 5,141,750; 5,314,694; and 5,342,623, the disclosures of which are incorporated in their entirety herein by reference.

When first investigated in depth in the late 1960's, the transdermal route of administration appeared to offer many advantages, particularly with respect to agents that had short half lives and therefore required frequent, repeated dosing or were subject to a high degree of first-pass metabolism by the liver when orally administered. The peaks and valleys in blood concentration resulting from frequent periodic doses of short half-life agents would be eliminated and replaced by substantially constant plasma concentration. This would not only improve individual compliance but also would eliminate the alternating periods of high side-effects and ineffective blood concentrations associated with period dosing. Administering the agent through the skin directly into the blood stream would also eliminate first-pass metabolism of orally administered agents.

It was initially assumed, theoretically, that any short half-life agent of high potency and skin permeability would be suitable for safe and effective transdermal administration. This assumption, however, has not been proven true.

The failure of the transdermal route to fulfill the initial expectations of its potential as an administrative portal was primarily due to the incredible variety of properties with which nature has endowed the skin to permit it to perform its function as the primary barrier to prevent the ingress of foreign substances into the body. See Transdermal Drug Delivery: Problems and Possibilities, B. M. Knepp, et al, CRC Critical Reviews and Therapeutic Drug Carrier Systems, Vol. 4, Issue 1 (1987) and Transdermal Delivery Systems: A Medical Rationale, Gary W. Cleary, *Topical Drug Bioavailability, Bioequivalence, and Penetration*, Plenum Press, 1993.

Thus, the transdermal route of administration, rather than being available to every short half-life agent of high potency and skin permeability, was found to be available only to those few agents that possess the proper combination of a host of characteristics, most of which are unpredictable, required to render the agent suitable for safe and effective transdermal administration.

The most significant of these characteristics are the following:

1. Skin Permeability. The permeability of the skin to the agent must be sufficiently high so that the agent can be administered at a therapeutically effective rate through an area of skin no greater than about 200 cm$^2$ and preferably no greater than 50 cm$^2$. The person-to-person variation in skin permeability at similar sites should also be considered. U.S. Pat. Nos. 4,568,343, 4,746,515, 4,863,738, 4,865,848, 4,888,354, 5,378,730, 5,641,504 and WO 95/09006, WO 95/01167, WO 96/37231, and WO 96/40259 are related to various compositions and methods for enhancing permeation of drugs through the skin and are hereby incorporated in their entirety by reference.

2. Skin Binding. The skin beneath the transdermal delivery device has the capability of creating a skin depot of drug by absorbing, adsorbing, or binding a certain amount of agent. The amount of agent so bound must be supplied to the skin before the agent can be delivered into the blood stream at steady, therapeutically effective rates. If large amounts of the agent are bound in the skin, significant delays in the onset of therapeutic effect ("lag time") will be observed together with corresponding delays and termination of effect upon removal of the device. The potential also exists for toxic quantities of potent agents to be contained within the skin beneath the device. Skin binding is not related to skin permeability. Agents that are highly permeable may also be highly bound causing a lag time sufficiently long as to render them unsuitable for their intended use.

3. Irritation. The skin reacts to many topically applied substances, particularly those maintained under occlusion, by blistering or reddening accompanied by unpleasant burning, itching, and stinging sensations. Animal models are used to screen for irritation. Animal models, however, often produce both false positives and false negatives. There is also a wide interpersonal variation in susceptibility to irritation. An agent must be minimally irritating in a large percentage of the potential individual population in order to be suitable for safe and effective transdermal administration. U.S. Pat. Nos. 4,552,872, 4,756,710, 5,028,431, 5,130,139, 5,160,741, and 5,451,407 are directed to overcoming problems associated with skin irritation associated with transdermal drug delivery and are hereby incorporated in their entirety by reference.

4. Sensitization. Sensitization is an allergic reaction which is induced when an agent is first applied to the skin and is elicited upon continued exposure which may occur immediately or after a long period of seemingly harmless exposure.

The sensitization may be local, elicited by topical exposure, which manifests itself as contact dermatitis accompanied by blistering, itching, reddening and burning at the site of application. More seriously, the sensitization may be systemic, elicited by topical application but manifesting itself by more general allergic reactions at sites other than the site of application. Most seriously, the systemic sensitization may be elicited by oral or intravenous administration of the drug. If the latter occurs, the individual will be unable to take the drug by any route of administration.

Animal models are used to screen for sensitization. Animal models, however, produce both false positives and false negatives. There is also a wide variation in the allergic reaction between individuals as well as between sexes, races and skin types. It is obvious that a useful transdermal agent must be minimally sensitizing in a large percentage of the potential individual population. U.S. Pat. Nos. 5,000,956, 5,049,387, 5,120,145, and 5,149,539 are directed to overcoming sensitization problems associated with transdermal drug delivery by the coadministration of a corticosteroid and are hereby incorporated in their entirety by reference 5. Pharmacokinetic Properties. The half-life of an agent is the time after administration that half of the amount administered has been eliminated from the body. Because blood concentrations of continuously administered agents will continue to increase for approximately five half-lives before steady-state constant blood concentrations are achieved, an agent must have a relatively short half-life to be suitable for continuous transdermal administration. The transdermal half-lives of most agents have not been determined. When half-lives of agents determined from intravenous administration are compared with half-lives determined from transdermal administration, the transdermal half-lives are generally longer but there can be wide variation in half-life between individuals based upon factors such as age, sex, health, and body type.

6. Pharmacodynamic Properties. Constant blood levels may not produce the desired therapeutic effects. For example, a therapeutic effect may only be observed at peak blood concentration obtained from bolus dosing but the peak blood or plasma concentration cannot be maintained because of side effects associated therewith. Also, continuous administration of many agents produces tolerance that may require either some agent-free interval or continually increasing and therefore potentially hazardous doses of the agent.

7. Potency. Although a certain degree of potency is required for transdermally administered agent to be effective, it is also possible for an agent to be too potent. As potency increases, lower blood concentrations are required and much smaller quantities are administered. Because of normal inter-individual variations and skin permeability, it may not be possible to precisely control whether a individual is receiving 1 $\mu$g/hr or 2 $\mu$g/hr, for example. For a highly potent agent, a 1 $\mu$g/hr administration may be totally ineffective and a 2 $\mu$g/hr rate fatal. Thus, the therapeutic index of an agent, which is the ratio of toxic blood concentration to the therapeutic blood concentration, becomes extremely significant. A highly potent agent should also have a relatively wide therapeutic window in order to be suitable for transdermal administration.

8. Metabolism. One of the perceived advantages of transdermal administration was that it avoided the "first-pass" metabolism of the agent by the liver that is associated with oral administration. It has now been recognized, however, that the skin is also a large metabolizing organ in the body for some drugs. Thus, although first-pass metabolism that occurs after an orally administered agent enters the blood stream can be avoided, skin metabolism, which occurs before the agent enters the bloodstream, cannot be avoided. Skin metabolism is capable of creating metabolites that are inert, irritating, toxic, or comparable in biological activity to that of the agent. An agent, to be suitable for transdermal administration, must have the metabolic properties that are consistent with its therapeutic use on continuous administration.

The above summarizes the primary characteristics that effect suitability of an agent for transdermal administration that have been recognized to date. There are undoubtedly others, some of which have not yet been recognized, and, in order for an agent to be suitable for transdermal administration, it must possess the right combination of all these characteristics, a combination of which, as illustrated by the very few drugs that are now suitable for administration from transdermal delivery devices, is quite rare and unpredictable.

DESCRIPTION OF TERMS

As used herein, the term "bioequivalents" intends that there is greater than 90% probability that the bioavailability is 80–125% and the minimum and maximum blood or plasma concentrations are 80–125% of the referenced dose.

As used herein, the term "fluoxetine" intends not only the basic form of fluoxetine but also pharmaceutically acceptable salt forms of fluoxetine, the R or S enantiomers of fluoxetine, either individually or as a racemic mixture, and to mixtures thereof.

As used herein, the term "fluoxetine therapy" intends all medical conditions for which fluoxetine is or will be indicated, including, without limitation, for the treatment of depression and obsessive-compulsive disorder.

As used herein, the term "individual" intends a living mammal and includes, without limitation, humans and other primates, livestock and sports animals such as cattle, pigs and horses, and pets such as cats and dogs.

As used herein, the term "irritation-reducing amount" intends an amount of an anti-irritant which reduces skin irritation throughout a substantial portion of the administration period.

As used herein, the term "permeation enhancement" intends an increase in the permeability of skin to fluoxetine and/or anti-irritant in the presence of a permeation enhancer as compared to permeability of skin to fluoxetine and/or anti-irritant in the absence of a permeation enhancer.

As used herein, the term "permeation enhancer" intends an agent or a mixture of agents which acts to increase the permeability of the skin to fluoxetine and/or anti-irritant.

As used herein, the term "permeation-enhancing amount" intends an amount of a permeation enhancer which provides permeation enhancement throughout a substantial portion of the administration period.

As used herein, the phrase "predetermined area of skin" intends a defined area of intact unbroken skin or mucosal tissue. That area will usually be in the range of about 5 cm$^2$ to about 100 cm$^2$.

As used herein the term "salt" intends, but is not limited to, pharmaceutically acceptable organic or inorganic salts. Typical inorganic salts include hydrogen halides such as hydrochlorides, carbonates, phosphates, sulfates, hydrogen sulfates, hydrobromides, nitrates, and sulfides. Organic salts includes, but are not limited to, acid addition salts including salts of monocarboxylic and polycarboxylic acids such as the acetate, maleate, and citrate.

As used herein, the phrase "sustained time period" or "administration period" intends at least about 8 hours and will typically intend a period in the range of about one to about seven days.

As used herein, the term "therapeutically effective amount" intends the dose of fluoxetine and/or its active metabolite, norfluoxetine, that provides fluoxetine therapy, in the case of adult and juvenile humans, the optimum dosage range is the equivalent of the oral dose of about 5–80 mg fluoxetine per day.

As used herein, the term "therapeutically effective rate" intends a rate of fluoxetine and/or its active metabolite, norfluoxetine, delivery effective to achieve therapeutic blood or plasma levels in an individual during the administration period and is typically within the range of 250–3200 µg/hr.

As used herein, the term "therapeutic blood or plasma level" intends the level of fluoxetine and/or its active metabolite, norfluoxetine, in blood or plasma that achieves a therapeutic effect for the desired fluoxetine therapy.

As used herein, the term "transdermal" intends both percutaneous and transmucosal administration, i.e., passage of fluoxetine through intact unbroken skin or mucosal tissue into the systemic circulation.

SUMMARY OF THE INVENTION

One aspect of this invention is directed to a method of transdermally administering a drug having a relatively long half-life.

Another aspect of this invention is provide sustained release formulations to administer a therapeutically effective amount of fluoxetine and/or its active metabolite, norfluoxetine, over an administration period.

More specifically, it is an aspect of this invention to provide compositions and methods for the transdermal delivery of fluoxetine and/or its active metabolites, and delivery systems for effecting the same, which are suitable for the transdermal administration of fluoxetine and/or its active metabolites continuously through a body surface or membrane at a therapeutically effective rate in order to achieve and maintain therapeutic blood or plasma levels in an individual.

Another aspect of this invention is to provide compositions, devices, and methods for transdermally administering fluoxetine at reduced skin irritation levels.

Another aspect of this invention is to improve patient compliance of patients in need of fluoxetine therapy by providing compositions, devices, and methods for the transdermal administration of fluoxetine at a therapeutically effective rate.

Yet another aspect of this invention is directed to compositions, devices, and methods for the transdermal administration of fluoxetine at reduced skin irritation levels together with a suitable permeation enhancer.

According to this invention, it has been discovered that fluoxetine can be safely and efficaciously administered transdermally at a therapeutically effective rate to provide, among other things, treatment for depression, when administered alone or when coadministered with a suitable permeation enhancer. A preferred embodiment is directed to transdermally administering a therapeutically effective amount of fluoxetine at reduced skin irritation levels wherein fluoxetine is coadministered from a transdermal drug delivery device containing a pharmaceutically acceptable salt of fluoxetine, an anti-irritant, and a permeation enhancer in order to provide systemic administration of fluoxetine.

These and other aspects of the present invention will be readily apparent from the description and accompanying figures that follow.

DETAILED DESCRIPTION OF THE INVENTION

One aspect of the invention is directed to a method of transdermal administration of an agent having a relatively long half-life, i.e. greater than about 24 hours. Previously, only agents having short half-lives were considered as suitable for transdermal administration. However, the present inventors have found that agents having such long half-lives may be advantageous for transdermal administration in that periodic missed doses would not be as likely to produce a fall in plasma drug levels below the minimum therapeutic blood or plasma level. Thus, it may be preferable to administer such drugs from a transdermal system which is placed onto the skin and maintained in drug transmitting relation for a first predetermined period of time and then replaced after a lapse of a second predetermined period of time of up to about 4 days. The first predetermined period of time is within 24–168 hours, preferably about 48–120 hours. The second predetermined period of time is within about 20–100 hours, preferably about 30–90 hours.

In addition to providing therapeutic blood or plasma levels for the period in which the device is applied to the skin, administration according to this embodiment is effective to maintain therapeutic blood or plasma levels of the agent in the patient throughout the period in which the system is not in drug transmitting relation with the skin of the patient. Although such a delivery regimen applies to any agent having the necessary half-life and therapeutic window, it will be described according to a preferred embodiment for delivering fluoxetine.

For example, one embodiment is directed to a system which contains an amount of fluoxetine effective to deliver fluoxetine at a therapeutically effective rate for approximately 3 days. The system would be worn for approximately three days and yet provide effective fluoxetine therapy throughout at least five days due to fluoxetine's long half-life. It is believed that such treatment regimens could improve patient compliance, particularly in individuals on maintenance therapy to prevent recurrent depression where fluoxetine therapy may be required for periods of five years or more.

To determine the administration regimen, an administration rate is determined by the relation:

$$\text{administration rate} = CL \cdot C_{ss} \tag{1}$$

where CL is the clearance and $C_{ss}$ is the steady state concentration of the drug.

The 90% steady state plasma concentration is the plateau concentration achieved by constant drug administration and is achieved by constant administration for approximately 3 to 4 half-lives of the drug. For example, a drug having a half life of 24 hours will have to be administered at a constant rate for approximately 4 days to reach 90% steady state. The drug concentration may be expressed in relation to the steady state concentration and the half life of the drug by the following expression:

$$C = C_{ss}[1 - (\tfrac{1}{2})^n] \tag{2}$$

where n=the number of half-lives elapsed since initiation of constant drug delivery.

Assuming that the drug input is stopped after achieving the upper limit of the therapeutic window, the time T it takes for the plasma concentration to drop to the lower limit of the therapeutic window is given by the following relation:

$$T = t_{1/2}/0.693 \cdot Ln\, C_U/C_L \tag{3}$$

wherein T=time for drug plasma concentration to drop from upper therapeutic window limit $C_U$ to its lower therapeutic window limit $C_L$. This relationship is shown in the Concentration vs. Time schematic below.

Thus, a steady state concentration is selected such that the resulting value for C derived by Equation (2) is within the therapeutic window for the drug and is sufficiently high to remain within the window throughout the period of no drug administration. The steady state concentration may be determined by one of ordinary skill in the art provided with values for drug clearance, half life, and therapeutic window.

For example, assuming a fluoxetine half-life of 48 hours, in order to maintain fluoxetine levels of 15–55 ng/mL, T is determined by equation (2) to be 90 hours. Thus, after achieving levels of 55 ng/mL, a system could then be removed while maintaining therapeutic levels for roughly 3.75 days. In the preferred embodiment directed to the administration of fluoxetine, the first predetermined period is preferably about 60–120 hours and the second predetermined period is preferably about 36–80 hours.

Examples of drugs having relatively long half-lives suitable for administration by this regimen include, but are not limited to, amiloride, amiodarone, amitriptyline, chloroquine, chlorpheniramine, chlorpromazine, chlorpropamide, chlorthalidone, clonazepam, dapsone, desipramine, nordazepam, diazepam, diazoxide, digitoxin, digoxin, doxepin, doxorubicin, doxycycline, ethosuximide, fluoxetine, flurazepam, furosemide, haloperidol, imipramine, nitrazepam, norfluoxetine, nortriptyline, paroxetine, phenylbutazone, phenytoin, pimozide, piroxicam, protriptyline, and warfarin.

In another aspect of this invention, it has been discovered that fluoxetine can be safely and efficaciously administered by a sustained release formulation. More specifically, it has been found that fluoxetine can be safely and efficaciously administered transdermally at a therapeutically effective rate to provide, among other things, treatment for depression, when administered alone or coadministered with a suitable permeation enhancer. The present invention provides novel compositions, devices, and methods for fluoxetine therapy with improved patient compliance to an individual in need of such therapy.

The present inventors have found that fluoxetine is moderately to severely irritating when administered transdermally as the base. A preferred embodiment of the present invention is therefore directed to providing compositions, devices, and methods for the transdermal administration of fluoxetine at reduced skin irritation levels. According to this preferred embodiment, a pharmaceutically acceptable salt of fluoxetine is coadministered with an anti-irritant, preferably a corticosteroid such as hydrocortisone. Particularly surprising is the discovery by the present inventors that a pharmaceutically acceptable salt of fluoxetine can be coadministered at therapeutically effective rates together with an anti-irritant and optionally, a permeation enhancer, from a single transdermal device in order to transdermally administer fluoxetine at reduced skin irritation levels throughout the administration period.

A particularly preferred embodiment is directed to the transdermal administration of fluoxetine acetate as the inventors have found that fluoxetine acetate may be transdermally administered at therapeutically effective rates and at reduced irritation levels without the use of permeation enhancers. Fluoxetine maleate is another preferred salt according to this invention but requires coadministration with a suitable permeation enhancer. Other salts which provide the necessary flux and irritation levels can be determined in accordance with the principles of the teachings of this invention.

Therapeutic blood or plasma levels can be obtained from administration rates in the range of 250–3200 $\mu$g/hr. Representative in vitro skin fluxes of fluoxetine through human skin are in the range of about 7–120 $\mu$g/cm$^2$·hr, depending on the drug form, permeation enhancer, and if an in-line adhesive is present.

The range of desired and achievable cumulative release of fluoxetine, arriving through the skin at a limited area is equivalent to the oral dosage of 10–80 mg per 24 hours. The system is easily adapted to provide a cumulative release of fluoxetine over a 24 hour period of less than 10 mg if necessary. Additionally, the system is easily adapted for shorter or longer duration treatments.

The desired fluoxetine administration rate may be achieved by increasing the surface area of the transdermal delivery device without increasing the flux. For example, for a fluoxetine skin flux of approximately 20 $\mu$g/cm$^2$·hr, the surface area of a patch would have to have a surface area of about 40 cm$^2$ in order to deliver approximately 19 mg of fluoxetine over a 24 hour period. The flux of fluoxetine through skin may also be increased by the use of permeation enhancers discussed below. A preferred embodiment of this invention relates to codelivery of a permeation enhancer to assist in the transdermal administration of fluoxetine and/or anti-irritant.

This invention finds particular usefulness in administering fluoxetine across skin. It is also useful, however, in administering fluoxetine across mucosa. According to the invention, fluoxetine is placed in fluoxetine transmitting relationship to an appropriate body surface, preferably in a pharmaceutically acceptable carrier thereof, and maintained in place for the desired administration period.

The fluoxetine, anti-irritant, and/or permeation enhancer, if used, are typically dispersed within a physiologically compatible matrix or carrier, as more fully described below, which may be applied directly to the body as an ointment, gel, cream, suppository or sublingual or buccal tablet. When used in the form of a liquid, ointment, lotion, cream or gel applied directly to the skin, it is preferable, although not required, to occlude the site of administration. Such compositions can also contain other permeation enhancers, stabilizers, dyes, diluents, pigments, vehicles, inert fillers, excipients, gelling agents, vasoconstrictors, and other components of topical compositions as are known to the art.

In other embodiments, fluoxetine would be administered from a transdermal delivery device as more fully described below. Examples of suitable transdermal delivery devices are illustrated in FIGS. 1–4. In the figures, the same reference numbers are used throughout the different figures to designate the same or similar components. The figures are not drawn to scale.

Figure 1:
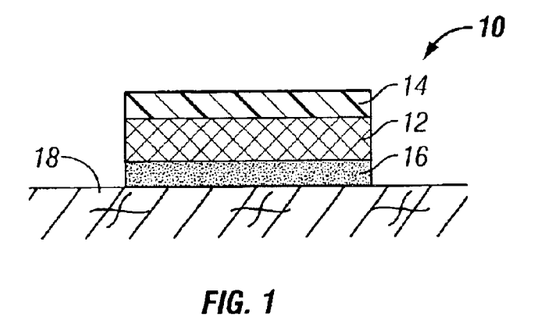
FIG. 1 is a cross-section through a schematic perspective view of one embodiment of a transdermal therapeutic system according to this invention.

Referring now to FIG. 1, a preferred embodiment of a transdermal therapeutic system according to this invention comprises transdermal delivery device 10 comprising a reservoir 12, preferably in the form of a matrix containing fluoxetine, anti-irritant, and a permeation enhancer dispersed therein. Reservoir 12 is sandwiched between a backing 14 and an in-line contact adhesive layer 16. The device 10 adheres to the surface of the skin 18 by means of the adhesive layer 16. The adhesive layer 16 may optionally contain the permeation enhancer, anti-irritant, and/or fluoxetine. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16. Additionally, a non-rate controlling tie layer membrane as disclosed in U.S. Pat. No. 5,635,203, incorporated herein it its entirety by reference, may be present between the reservoir 12 and adhesive 16 in any of the embodiments depicted in FIGS. 1–4.

Although the preferred embodiments of this invention utilize an in-line adhesive as is shown in FIG. 1, other means for maintaining the system on the skin can be employed. Such means include a peripheral ring of adhesive outside the path of the drug from the system to the skin or the use of other fastening means such as buckles, belts, and elastic arm bands.

Alternatively, reservoir 12 may be in the form of a matrix containing fluoxetine, anti-irritant, and permeation enhancer, if used, dispersed within a suitable adhesive, preferably a pressure sensitive adhesive. Such pressure sensitive adhesives include, but are not limited to, polysiloxanes, polyacrylates, polyurethanes, acrylic adhesives including cross linked or uncross linked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof. The matrix formulations according to this embodiment comprise the adhesive containing fluoxetine, anti-irritant, and permeation enhancer, if present, laminated to a backing on one surface and to a release liner on the other. In addition to the fluoxetine, anti-irritant, and permeation enhancer, the matrix or carrier may also contain dyes, pigments, inert fillers, excipients and other conventional components of pharmaceutical products or transdermal devices known to the art. For example, the matrix may also be provided with hydrophilic water absorbing polymers known in the art such as polyvinyl alcohol and polyvinyl pyrrolidone individually or in combination.

Figure 2:
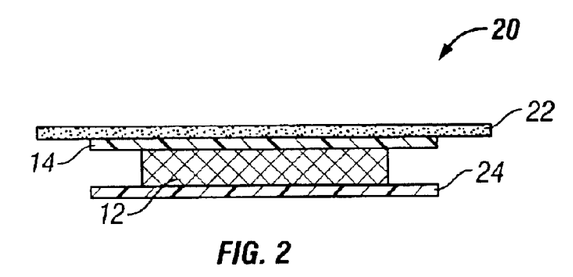
FIG. 2 is a cross-section view through another embodiment of this invention prior to application to the skin.

Alternatively, as shown in FIG. 2, transdermal therapeutic device 20 may be attached to the skin or mucosa of a patient by means of an adhesive overlay 22. Device 20 is comprised of reservoir 12 preferably in the form of a matrix containing fluoxetine, anti-irritant, and a permeation enhancer dispersed therein. A backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

Figure 3:
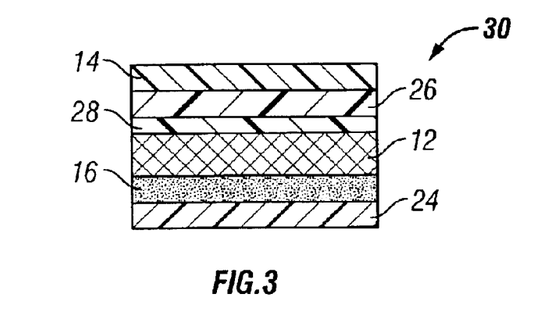
FIG. 3 is a cross-section view through another embodiment of this invention prior to application to the skin.

In FIG. 3, transdermal delivery device 30 comprises a fluoxetine, anti-irritant, and permeation enhancer reservoir ("fluoxetine reservoir") 12 substantially as described with respect to FIG. 1. Permeation enhancer reservoir ("enhancer reservoir") 26 comprises the permeation enhancer dispersed throughout and contains fluoxetine at or below saturation, when in equilibrium with the fluoxetine reservoir 12. Enhancer reservoir 26 is preferably made from substantially the same matrix as is used to form fluoxetine reservoir 12. A rate-controlling membrane 28 for controlling the release rate of the permeation enhancer from enhancer reservoir 26 to fluoxetine reservoir 12 is placed between the two reservoirs. A rate-controlling membrane (not shown in FIG. 3) for controlling the release rate of the enhancer, anti-irritant, and/or fluoxetine from fluoxetine reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate, ethylene n-butyl acetate and ethylene vinyl acetate copolymers.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low-viscosity flowable material such as a liquid or a gel, the composition can be fully enclosed in a pouch or pocket, as known to the art from U.S. Pat. No. 4,379,454 (noted above), for example, and as illustrated in FIG. 4. Device 40 shown in FIG. 4 comprises a backing member 14 which serves as a protective cover for the device, imparts structural support, and substantially keeps components in device 40 from escaping the device. Device 40 also includes reservoir 12, which contains the fluoxetine and any anti-irritant and/or permeation enhancer and bears on its surface distant from backing member 14, a rate-controlling membrane 28 for controlling the release of fluoxetine, anti-irritant, and/or permeation enhancer from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

Figure 4:
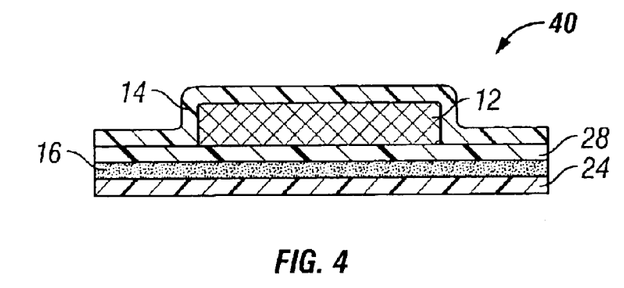
FIG. 4 is a cross-section view through another embodiment of this invention prior to application to the skin.

In an alternative embodiment of device 40 of FIG. 4, reservoir 12 contains the permeation enhancer and anti-irritant and contains fluoxetine at or below saturation. The fluoxetine and an additional amount of permeation enhancer and/or anti-irritant are present in adhesive layer 16, which acts as a separate reservoir.

Fluoxetine can be administered to human skin or mucosa by direct application to the skin or mucosa in the form of an ointment, gel, cream or lotion, for example, but are preferably administered from a skin patch or other known transdermal delivery device which contains a saturated or unsaturated formulation of the fluoxetine and any anti-irritant and/or enhancer. The formulation may be aqueous or non-aqueous based. The formulation should be designed to deliver the fluoxetine and any anti-irritant and/or enhancer at the necessary fluxes. Aqueous formulations typically comprise water or water/ethanol and about 1–5 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with the fluoxetine, anti-irritant, and the permeation enhancer, if used, in addition to any other components in the formulation.

The reservoir matrix should be compatible with fluoxetine, the permeation enhancer, and any carrier therefor. The term "matrix" as used herein refers to a well-mixed composite of ingredients. When using an aqueous-based formulation, the reservoir matrix is preferably a hydrophilic polymer, e.g., a hydrogel.

When using a non-aqueous based formulation, the reservoir matrix is preferably composed of a hydrophobic polymer. Suitable polymeric matrices are well known in the transdermal drug delivery art, and examples are listed in the above-named patents previously incorporated herein by reference. A typical laminated system would consist essentially of a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 9% to 40% VA. Polyisobutylene/oil polymers containing from 4–25% high molecular weight polyisobutylene and 20–81% low molecular weight polyisobutylene with the balance being an oil such as mineral oil or polybutene may also be used as the matrix material.

The amount of fluoxetine present in the therapeutic device and required to achieve an effective therapeutic result depends on many factors, such as the minimum necessary dosage of the fluoxetine for the particular indication being treated; the solubility and permeability of the matrix, taking into account the presence of an anti-irritant, permeation enhancer, of the adhesive layer and of the rate-controlling membrane, if present; and the period of time for which the, device will be fixed to the skin. The minimum amount of fluoxetine is determined by the requirement that sufficient quantities of fluoxetine must be present in the device to maintain the desired rate of release over the given period of application. The maximum amount for safety purposes is determined by the requirement that the quantity of fluoxetine present cannot exceed a rate of release that reaches toxic levels.

The fluoxetine may be present in the matrix or carrier at a concentration at or below saturation. An excess amount of fluoxetine above saturation may be included in the matrix or carrier, the amount of excess being a function of the desired length of the delivery period of the system. Fluoxetine may be present at a level below saturation without departing from this invention as long as it is continuously administered to the skin or mucosal site at a therapeutic rate and for a period of time sufficient to deliver a therapeutically effective amount of fluoxetine that provides the desired therapeutic result.

The permeation enhancer useful in the present invention is selected from those compounds which are compatible with fluoxetine and which provide enhanced skin permeation to the drug when it is administered together with the drug to the skin of a user. Additionally, the permeation enhancer must not adversely interact with the adhesive of the in-line contact adhesive layer if one is present. Examples of permeation enhancers are disclosed in the patents cited above previously incorporated by reference and can be selected from, but are not limited to, fatty acids, monoglycerides of fatty acids such as glycerol monolaurate, glycerol monooleate or glycerol monolinoleate; lactate esters of fatty acids such as lauryl lactate, cetyl lactate, and myristyl lactate; acyl lactylates such as caproyl lactylic acid; lauramide diethanolamine (LDEA); esters of fatty acids having from about 10 to about 20 carbon atoms including lauryl acetate; alkyl laurates such as methyl laurate; dimethyl lauramide; isopropyl myristate; polyethylene glycol-4 lauryl ether (Laureth-4); polyethylene glycol monolaurate; and lower $C_{1-4}$ alcohols such as isopropanol and ethanol, alone or in combinations of one or more.

A preferred permeation enhancer according to this invention comprises a monoglyceride of a fatty acid together with a suitable cosolvent, including, but not limited to, fatty acids esters such as lauryl lactate, lauryl acetate, and methyl laurate. Methyl laurate has been found to be particularly desirable as it is obtainable at a high degree of purity, thus providing a purer and better defined permeation enhancer and a system which is more readily characterized. According to a particularly preferred embodiment, the permeation enhancer comprises glycerol monolaurate (GML) and methyl laurate within the range of 1–25 wt % and 1–20 wt %, respectively, at a ratio of GML/methyl laurate within the range of 0.5–5.0, preferably 1.0–3.5.

The permeation-enhancing mixture is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

The anti-irritant is dispersed throughout the matrix or carrier, preferably at a concentration sufficient to deliver anti-irritant to the skin in an amount effective to reduce skin irritation throughout the anticipated administration period. The anti-irritant is preferably present in excess of saturation in order to provide that the anti-irritant is continuously administered with the fluoxetine and continues to be present as long as any fluoxetine is present in the epidermis. Suitable anti-irritants include, but are not limited to, methyl nicotinate as disclosed in U.S. Pat. No. 5,451,407, corticosteroids, and buffering agents including ascorbic acid and acetic acid. Such anti-irritants are known in the art as seen in the above cited patents previously incorporated by reference.

According to a preferred embodiment, the anti-irritant is a corticosteroid and is preferably administered at a flux within the range of 0.1–5.0 $\mu g/cm^2 \cdot hr$. Hydrocortisone is the preferred corticosteroid. The total amount of hydrocortisone administered is not to exceed 5 mg/24 hour in order to avoid possible systemic effects. Hydrocortisone esters such as hydrocortisone acetate are also suitable. More potent corticosteroids may not require a permeation enhancer as hydrocortisone and hydrocortisone acetate do. However, the advantages of hydrocortisone or its esters such as hydrocortisone acetate is that they are approved for over-the-counter use. This invention contemplates the use of any corticosteroid in addition to hydrocortisone and includes, without limitation, beclomethasone, betamethasone, benzoid, betamethasone dipropionate, betamethasone valerate, clobetasol propionate, clobetasol butyrate, desonide, dexamethasone, fluocinonide, prednisolone, and triamcinolone, for example.

Because of the wide variation in skin permeability from individual to individual and from site to site on the same body, it may be preferable that the fluoxetine, anti-irritant, and/or permeation enhancer, be administered from a rate-controlled transdermal delivery device. Rate control can be obtained either through a rate-controlling membrane as described in U.S. Pat. No. 3,797,494 listed above, or through an adhesive or both as well as through other means known in the art.

A certain amount of fluoxetine will bind reversibly to the skin, and it is accordingly preferred that the skin-contacting layer of the device include this amount of fluoxetine as a loading dose.

The surface area of the device of this invention can vary from about 1–200 $cm^2$. A typical device, however, will have a surface area within the range of about 5–60 $cm^2$, preferably about 20 $cm^2$.

The devices of this invention can be designed to effectively deliver fluoxetine for an extended time period of from several hours up to 7 days or longer. Seven days is generally the maximum time limit for application of a single device because the adverse affect of occlusion of a skin site increases with time and the normal cycle of sloughing and replacement of the skin cells occurs in about 7 days.

Preferably, a device for the transdermal administration of fluoxetine, at a therapeutically effective rate, comprises:
  (a) a reservoir comprising:
    (i) 1–50% by weight fluoxetine,
    (ii) 0.01 to 10% by weight anti-irritant,
    (iii) 30 to 90% by weight of a polymeric carrier;
  (b) a backing behind the skin-distal surface of the reservoir; and
  (c) means for maintaining the reservoir in fluoxetine— transmitting relation with the skin.

More preferably, a device for the transdermal administration of fluoxetine, at a therapeutically effective rate, comprises:
  (a) a reservoir comprising:
    (i) 1–50% by weight of a pharmaceutically acceptable salt of fluoxetine,
    (ii) 0.01 to 10% by weight anti-irritant,
    (iii) 1–50% by weight of a permeation enhancer,
    (iv) 30–90% by weight of a polymeric carrier;
  (b) a backing behind the skin-distal surface of the reservoir; and (c) means for maintaining the reservoir in fluoxetine—transmitting relation with the skin.

Most preferably, a device for the transdermal administration of fluoxetine, at a therapeutically effective rate, comprises:

(a) a reservoir comprising:
  (i) 10–50% by weight of a pharmaceutically acceptable salt of fluoxetine,
  (ii) 0.1 to 10% by weight corticosteroid,
  (iii) 10–50% by weight of a permeation enhancer,
  (iv) 30–90% by weight of a polymeric carrier;
(b) a backing behind the skin-distal surface of the reservoir; and
(c) means for maintaining the reservoir in fluoxetine, corticosteroid, and permeation enhancer—transmitting relation with the skin.

The backing may be flexible or nonflexible and may be a breathable or occlusive material. Suitable materials include, without limitation, polyethylene, polyurethane, polyester, ethylene vinyl acetate, acrylonitrile, cellophane, cellulose acetate, cellulosics, ethylcellulose, ethylene vinyl alcohol, plasticized vinylacetate-vinylchloride copolymers, polyethylene terephthalate, nylons, rayon, polypropylene, polyvinyl alcohol, polyvinyl chloride, metalized polyester films, polyvinylidene chloride, polycarbonate, polystyrene, and aluminum foil. The backing may be a multi-laminate film.

The means for maintaining the reservoir in drug and permeation enhancer transmitting relation with the skin is preferably a pressure sensitive adhesive including, but not limited to, polyisobutylene adhesives, silicone adhesives, and acrylate adhesives known in the art including copolymers and graft copolymers thereof. A further embodiment of the invention is directed to including in the adhesive a small percentage, e.g., from about 1 to about 5 wt % of fluoxetine to assure an appropriate initial release rate.

The aforementioned patents describe a wide variety of materials which can be used for fabricating various layers or components of the transdermal fluoxetine delivery systems according to this invention. This invention, therefore, contemplates the use of other materials other than those specifically disclosed herein including those which may become hereafter known to the artist capable of forming the necessary functions.

The invention is also directed to a method of continuously administering fluoxetine and/or norfluoxetine to a patient at a therapeutically effective rate over an administration period in order to administer a therapeutically effective amount and achieve and maintain therapeutic blood or plasma levels in a patient.

Another method of the present invention is directed to a method for the transdermal coadministration of fluoxetine and/or norfluoxetine at a therapeutically effective rate together with an irritation reducing amount of an anti-irritant in order to achieve and maintain therapeutic blood or plasma levels in a patient, comprising:

(a) coadministering to a body surface or membrane, fluoxetine and/or norfluoxetine; and
(b) an anti-irritant, wherein a therapeutically effective amount of fluoxetine is delivered at a therapeutically effective rate during an administration period in order to achieve and maintain therapeutic blood or plasma levels in a patient. The fluoxetine and anti-irritant may be administered to the body surface or membrane by means of the devices and compositions described above.

A preferred embodiment of the present invention comprises a method of treating depression. To achieve this result, fluoxetine is delivered at a therapeutic rate within a range of about 250–3200 μg/hr, preferably at about 400–1200 μg/hr from a reasonably sized transdermal delivery device having a surface area of less than about 60 cm$^2$ for the treatment period, usually about 12 hours to 5 days.

The length of time of fluoxetine presence and the total amount of fluoxetine in the plasma can be changed following the teachings of this invention to provide different treatment regimens. Thus, they can be controlled by the amount of time during which exogenous fluoxetine is delivered transdermally to an individual or animal and the rate at which it is administered.

Having thus generally described our invention, the following specific examples describe preferred embodiments thereof but are not intended to limit the invention in any manner.

EXAMPLE 1

Several test samples were made to measure the flux of fluoxetine base through human cadaver epidermis from donor vehicles containing 10% by weight fluoxetine base in an oil/petrolatum carrier with 0–10% by weight glycerol monolaurate (GML) as shown in Table 1.

TABLE 1

| Symbol (FIG. 5) | Non-Aqueous Donor Solutions (weight percent) | | |
| --- | --- | --- | --- |
| | Fluoxetine | GML | Oil/Petrolatum |
| ■ | 10 | 0 | 90 |
| ● | 10 | 2.5 | 87.5 |
| ▲ | 10 | 5 | 85 |
| ⊞ | 10 | 10 | 80 |

The experiment was carried out using standard glass diffusion cells which consist of a donor compartment with a 7.5 ml capacity, and a receptor compartment with a 22 ml capacity. A circular piece of epidermis was placed in each diffusion cell (permeation area=2.27 cm$^2$) in a horizontal position between a lower capped receptor compartment and an upper capped donor compartment. The receptor compartment has both a venting tube (uncapped) and a sampling port (capped). The stratum corneum side of the epidermis faced the donor compartment. An O-ring was positioned between the epidermis and the donor compartment, and a clamp held the compartments together. The receptor solution, 22 ml of 0.001 M phosphoric acid solution, pH 3.2, was added to each receptor compartment. The cells were placed in a temperature controlled water bath shaker at 35° C. and allowed to come to temperature before the donor solution was added.

At each time interval, the receptor solution was removed from the test cell and replaced with an equal volume of fresh receptor solution previously equilibrated at 35° C. The receptor solutions for each time interval were then assayed for fluoxetine by HPLC (Metachem Inertsil, ODS3, 15 cm×2.0 mm ID, 5 μm, Mobile phase: 35% acetonitrole/64.25% water, 0.50% triethylamine, 0.25% H$_3$PO$_4$ (85%), 244 nm, 0.3 ml/min) to calculate the permeation rate of fluoxetine through epidermis from the donor solutions. From the drug concentration and the volume of the receptor solutions, the area of permeation and the time interval, the flux of the drug through the epidermis was calculated as follows: (drug concentration×volume of receptor)/(area×time)=flux (μg/cm$^2$·hr).

Figure 5:
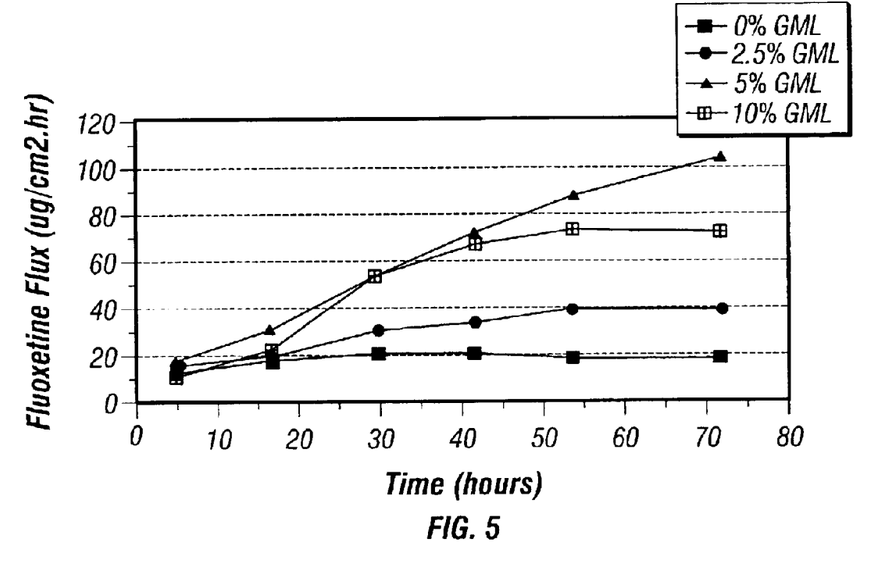
FIG. 5 is a graph depicting the flux of fluoxetine base through epidermis from oil/petrolatum formulations with varying amounts of GML.

FIG. 5 graphically depicts the results. As seen in FIG. 5, the average baseline skin flux of fluoxetine base without any permeation enhancer is approximately 20 $\mu g/cm^2 \cdot hr$ over a seventy two hour period. The addition of GML acted to increase the fluoxetine flux from two to five fold.

EXAMPLE 2

Figure 6:
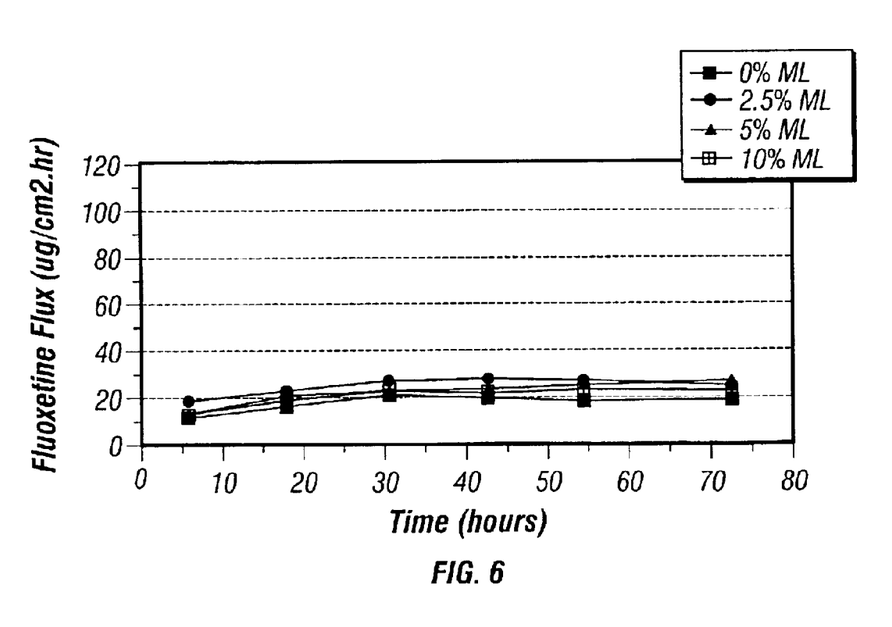
FIG. 6 is a graph depicting the flux of fluoxetine base through epidermis from oil/petrolatum formulations with varying amounts of methyl laurate.

Several test samples were made to measure the flux of fluoxetine base through human cadaver epidermis from donor vehicles containing 10% by weight fluoxetine base in an oil/petrolatum carrier with 0–10% by weight methyl laurate (ML) as shown in Table 2. Transdermal fluxes were obtained using human epidermis at 35° C. in standard diffusion cells using the procedure set forth in Example 1. FIG. 6 graphically depicts the results. As seen in FIG. 6, methyl laurate by itself did not significantly increase the fluoxetine flux.

TABLE 2

Non-Aqueous Donor Solutions (weight percent)

| Symbol (FIG. 6) | Fluoxetine | ML | Oil/Petrolatum |
|---|---|---|---|
| ■ | 10 | 0 | 90 |
| ● | 10 | 2.5 | 87.5 |
| ▲ | 10 | 5 | 85 |
| ⊞ | 10 | 10 | 80 |

EXAMPLE 3

Figure 7:
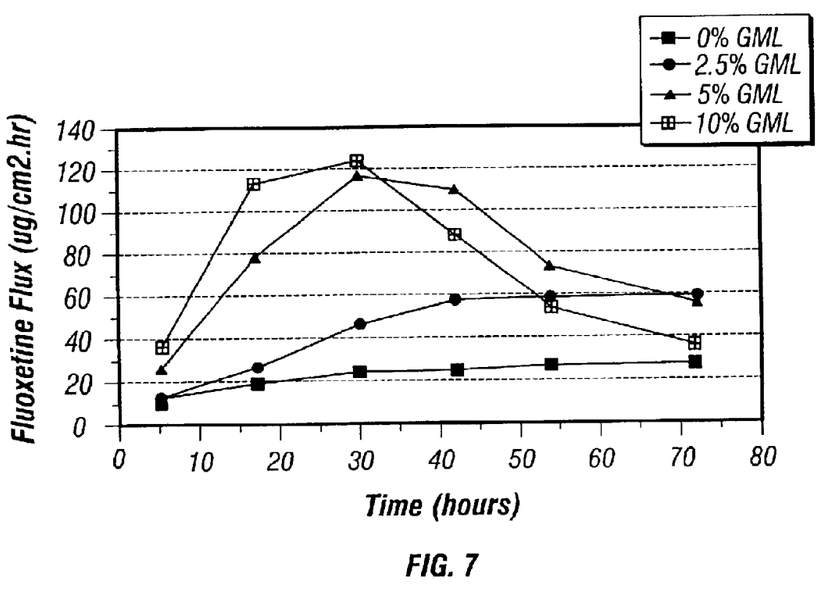
FIG. 7 is a graph depicting the flux of fluoxetine base through epidermis from oil/petrolatum formulations with varying amounts of GML and 5% methyl laurate.

Several test samples were made to measure the flux of fluoxetine base through human cadaver epidermis from donor vehicles containing 10% by weight fluoxetine base in an oil/petrolatum carrier with 5% by weight methyl laurate (ML) and 0–10% by weight GML as shown in Table 3. Transdermal fluxes were obtained using human epidermis at 35° C. in standard diffusion cells using the procedure set forth in Example 1. As seen in FIG. 7, the combination of methyl laurate and GML exhibited a synergistic effect on the flux of fluoxetine as compared to the enhancement of flux in the presence of GML or methyl laurate individually.

TABLE 3

Non-Aqueous Donor Solutions (weight percent)

| Symbol (FIG. 7) | Fluoxetine | GML | ML | Oil/Petrolatum |
|---|---|---|---|---|
| ■ | 10 | 0 | 5 | 85 |
| ● | 10 | 2.5 | 5 | 82.5 |
| ▲ | 10 | 5 | 5 | 80 |
| ⊞ | 10 | 10 | 5 | 75 |

EXAMPLE 4

Fluoxetine irritation and flux were studied in hairless guinea pigs. Formulations containing 30% (vol/vol) ethanol, 45% (vol/vol) propylene glycol, water, and fluoxetine base and acetate at various concentrations (% wt/vol) as shown in Table 4 were mixed together with $^3$H fluoxetine at a final concentration of 24 $\mu$Ci/mL and gelled with 4% methylcellulose.

Skin sites on hairless guinea pigs were lightly washed. 2 cm$^2$ systems were filled with 350 $\mu$L of the gel formulation. One radioactive gel and one placebo gel (no drug) was applied to each guinea pig on opposite sides of the animal (n=3 per group) and an adhesive overlay was placed over each system. The guinea pigs were wrapped with Vetwrap™ and returned to metabolic cages. The systems were removed after 24 hours and the sites were thoroughly washed and marked. Photos and skin evaluations were taken at 2, 24, and 48 hours post-removal and were assessed according to the method of Draize et al. Urine was collected daily for 7 days and analyzed for radioactive content by scintillation counting. The fluoxetine flux was calculated from the urinary excretion data and was corrected by the percent urinary elimination following intracardiac administration of fluoxetine. The results, represented as an average for each formulation tested, are listed in Table 4.

TABLE 4

PII v. flux for various fluoxetine base/acetate formulations

| | Fluoxetine | % Fluoxetine (wt/vol) expressed as base | Fluoxetine flux ($\mu g/cm^2 \cdot hr$) | PII |
|---|---|---|---|---|
| Gel A | 0.15 M base | 4.6 | 50.8 | 6.8 |
| Gel B | 0.075 M base | 2.3 | 12.2 | 3.3 |
| Gel C | 0.0375 M base | 1.16 | 5.0 | 1.7 |
| Gel D | 0.328 M acetate | 10.1 | 10.5 | 1.0 |
| Gel E | 0.164 M acetate | 5.1 | 3.6 | 0.7 |
| Gel F | 0.082 M acetate | 2.5 | 2.4 | 0.3 |
| Gel G | none | 0 | — | 0.3 |

EXAMPLE 5

The drug/permeation enhancer reservoirs were prepared by mixing ethylene vinyl acetate having a vinyl acetate content of 40 percent ("EVA 40", USI Chemicals, Illinois), with fluoxetine acetate, hydrocortisone base (HC), GML, and a cosolvent comprising lauryl lactate (LL), dodecyl acetate (DA), or methyl laurate (ML) in a "Brabender" type mixer as set forth in Table 5. After blending, the mixture was calendered into a 6 mil. thick film. The film was then laminated to a 1 mil. unsiliconized polyethylene backing on one side. The composition of the drug reservoirs is shown in Table 5.

TABLE 5

Drug/Permeation Enhancer Reservoir Composition (weight percent).

| Sample # | Formulation | Weight Percent |
|---|---|---|
| 1 | fluoxetine acetate/EVA/HC/GML/ML | 33/47/5/10/5 |
| 2 | fluoxetine acetate/EVA/HC/GML/DA | 33/47/5/10/5 |
| 3 | fluoxetine acetate/EVA/HC/GML/LL | 33/47/5/10/5 |
| 4 | fluoxetine acetate/EVA/HC | 33/62/5 |
| 5 (control) | fluoxetine base/EVA | 33/67 |

Circular pieces of human epidermis were placed with stratum corneum facing up. The release liner of the laminate was removed and the fluoxetine releasing side of the system was centered over the stratum corneum side of the epidermis which had been blotted dry just prior to use. The edges of epidermis were then folded around the system so that none of the system edge was exposed to the receptor solution. This assembly was then mounted on a Teflon® holder of a release rate rod using nylon mesh and metal string. A known volume of receptor solution (0.001 M $H_3PO_4$) was then placed in a test tube and was equilibrated at 35° C. The test tube was placed in a water bath and maintained at 35° C. The Teflon rod with system and epidermis attached was then reciprocated within the test tube by attaching the rod to a motor which caused constant vertical mixing.

Figure 8:
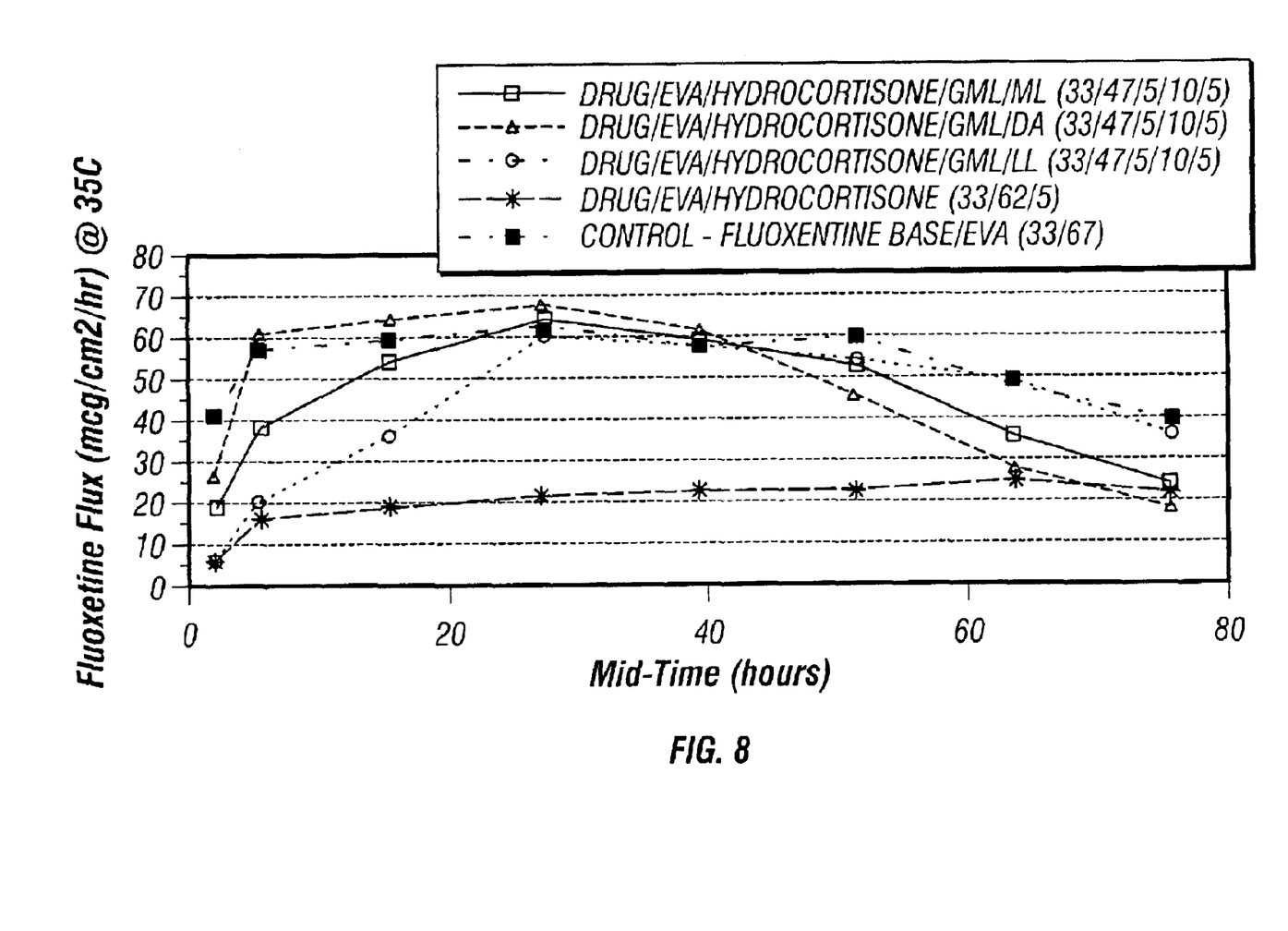
FIG. 8 is a graph depicting the flux of fluoxetine acetate through epidermis from EVA systems with various permeation enhancers.
Figure 9:
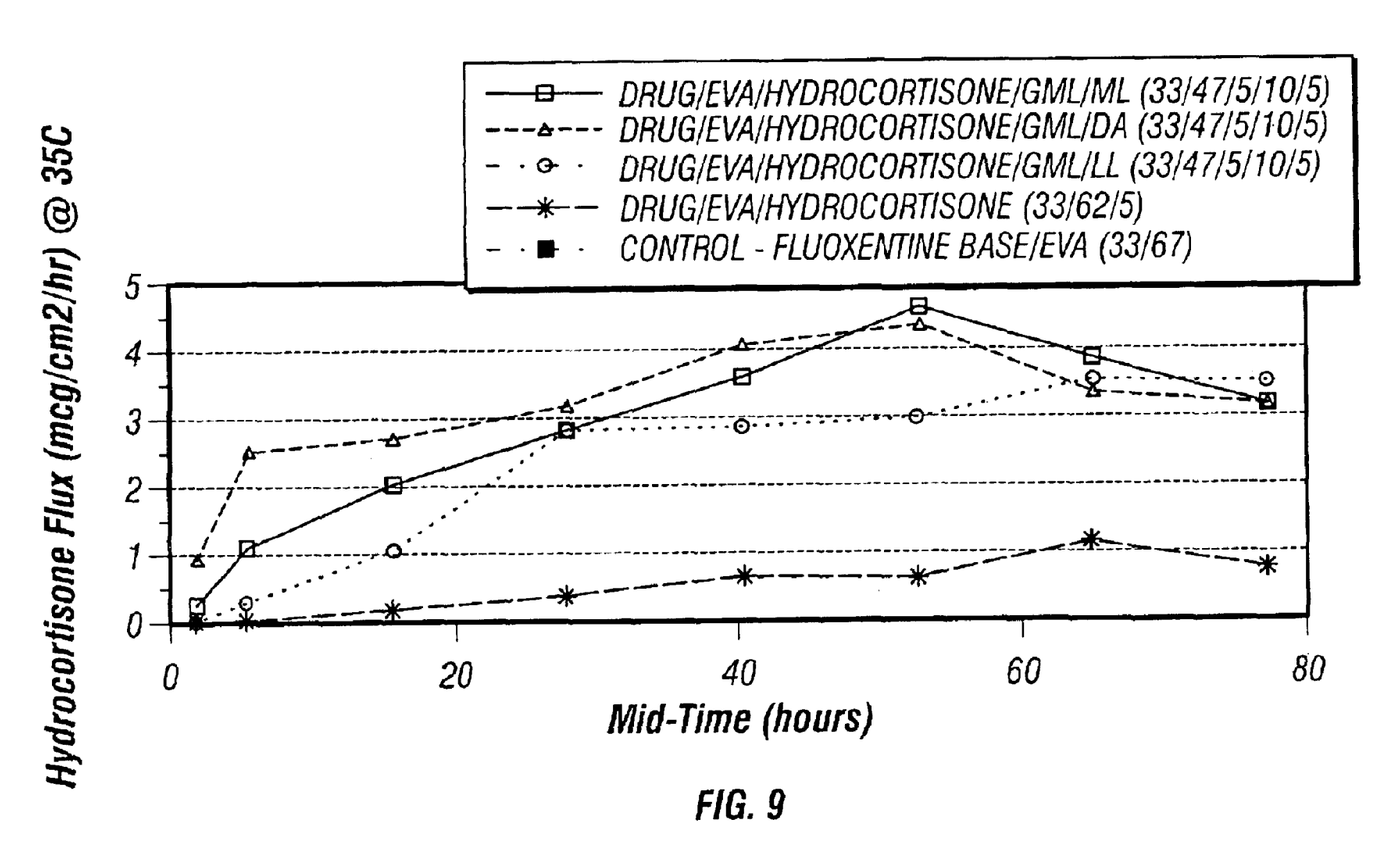
FIG. 9 is a graph depicting the flux of hydrocortisone through epidermis from EVA systems containing fluoxetine acetate with various permeation enhancers.

At given time intervals, the entire receptor solution was removed from the test tubes and replaced with an equal volume of fresh receptor solutions previously equilibrated at 35° C. The receptor solutions are stored in capped vials at 4° C. until assayed for fluoxetine content by HPLC. From the drug concentration and the volume of the receptor solutions, the area of permeation and the time interval, the flux of the drug through the epidermis was calculated as follows: (drug concentration×volume of receptor)/(area×time)=flux ($\mu$g/cm$^2$·hr). The in vitro flux of fluoxetine acetate through epidermis at 35° C. is shown in FIG. 8. The in vitro flux of hydrocortisone through epidermis at 35° C. is shown in FIG. 9.

EXAMPLE 6

Drug reservoirs containing fluoxetine acetate, fluoxetine hydrochloride, or fluoxetine maleate were prepared according to the procedure set forth in Example 5. An adhesive layer was laminated to some of the drug reservoir laminates. The laminate formulations are set forth in Table 6. The acrylate adhesive used was a 2 mil layer of Acrylate #73–9259 (National Starch, Bridgewater, N.J.). The PIB was a mixture of 90 wt % low molecular weight PIB (MW 35,000) and 10 wt % high molecular weight PIB (MW 1,200,000) with a 1 mil thickness.

TABLE 6

Drug/Permeation Enhancer Reservoir Composition (weight percent).

| Sample # | Formulation | Adhesive | Weight Percent |
|---|---|---|---|
| 1 | fluoxetine acetate/EVA/HC | acrylate | 33/62/5 |
| 2 | fluoxetine acetate/EVA | acrylate | 33/67 |
| 3 | fluoxetine acetate/EVA/HC | PIB | 33/62/5 |
| 4 | fluoxetine acetate/EVA | PIB | 33/67 |
| 5 | fluoxetine hydrochloride/EVA/GML/DA/HC | acrylate | 33/47/10/5/5 |
| 6 | fluoxetine hydrochloride/EVA/GML/DA | acrylate | 33/52/10/5 |
| 7 | fluoxetine maleate/EVA/GML/DA/HC | none | 33/47/10/5/5 |
| 8 | fluoxetine maleate/EVA/GML/DA | none | 33/52/10/5 |

Skin fluxes were obtained using the procedure set forth in Example 5. Average skin fluxes (average of 2 skins) over a 72 hour period are given in Table 7. Additionally, skin irritation was measured in a three day wear study conducted on hairless guinea pigs. Irritation was observed at ½ hour, 24 hours, and 48 hours after removal of the systems. Primary irritation index (PII) scores were determined using the Draize et al. method and are given in Table 7.

TABLE 7

Average Skin Flux and Primary Irritation Index Scores

| Sample | Average Flux ($\mu$g/cm$^2$ · hr) | PII Score |
|---|---|---|
| 1 | 12 | 1.4 |
| 2 | 13 | 3.1 |
| 3 | 10 | 4.4 |
| 4 | 18 | 5.9 |
| 5 | 8 | 4.3 |
| 6 | 9 | 4.5 |
| 7 | 19 | 1.6 |
| 8 | 17 | 2.4 |

EXAMPLE 7

Figure 10:
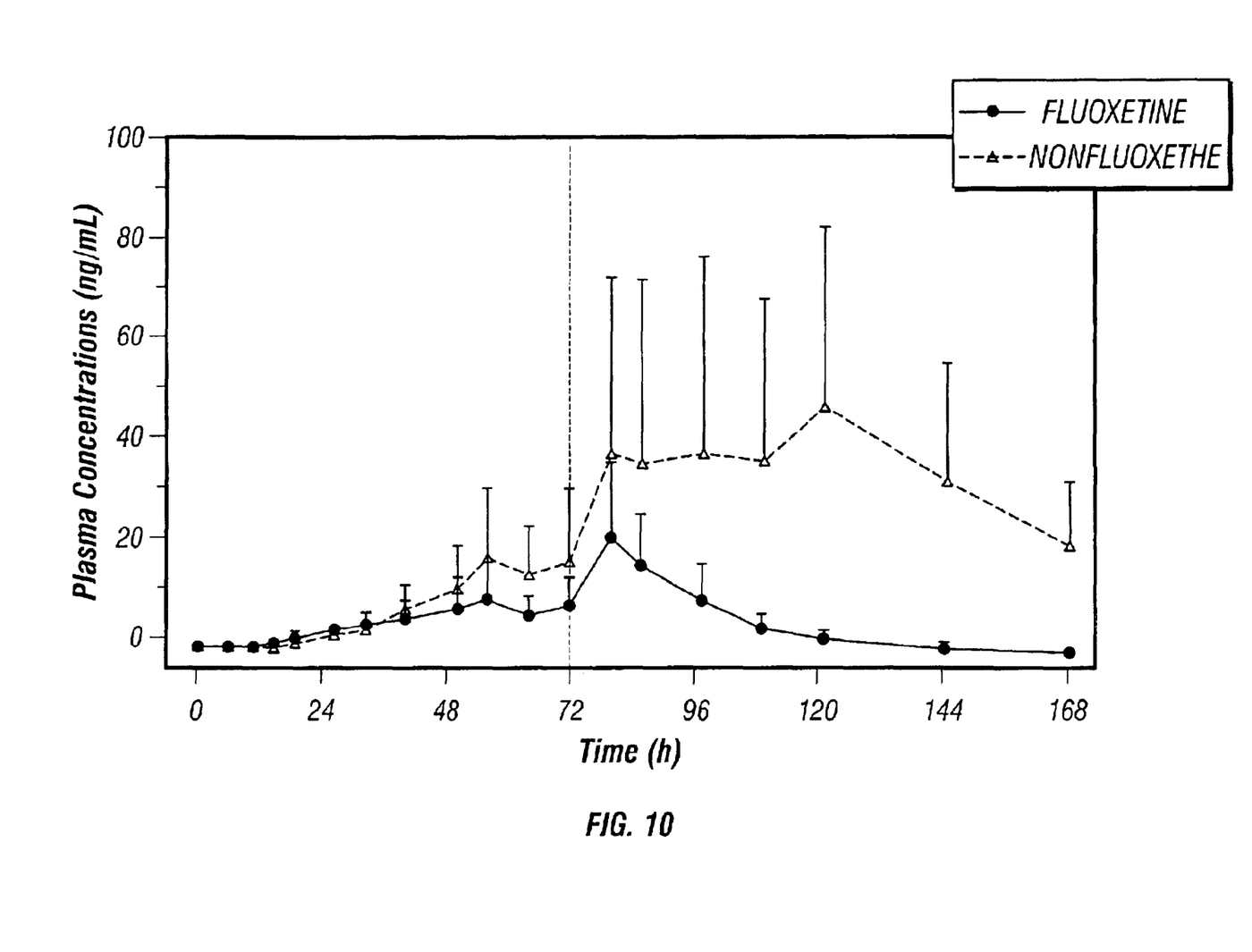
FIG. 10 is a graph depicting fluoxetine and norfluoxetine plasma concentrations.

A pharmacokinetic study was conducted on beagels (n=6) to observe fluoxetine and norfluoxetine plasma levels. 60 cm$^2$ systems containing the formulation identified as sample 1 of Example 6 were prepared according to the procedure set forth in Example 5. One patch was applied for a 72 hour period to each of the 6 beagels at a site which had been cleaned and shaved prior to application of the system. Blood samples were collected predose, 4, 8, 12, 16, 24, 30, 38, 48, 54, 62, and 72 hours after system application, and at 6, 12, 24, 36, 48, 72, and 96 hours after system removal. The heparinized plasma samples were frozen and sent to Simbec Research Limited, So. Wales, UK for fluoxetine and norfluoxetine assay by gas chromatograph—electron capture detection (GC-ECD). The results are shown in FIG. 10, which shows that norfluoxetine levels remained at 96 hours after system removal after a 3 day application.

Having thus generally described our invention and described certain specific embodiments thereof, including the embodiments that applicants consider the best mode of practicing their invention, it should be readily apparent that various modifications to the invention may be made by workers skilled in the art without departing from the scope of this invention which is limited only by the following claims.

Wherein, what is claimed is:

1. A device for the transdermal administration of fluoxetine at a therapeutically effective rate, comprising:
   (a) a first reservoir comprising an amount of a pharmaceutically acceptable salt of fluoxetine;
   (b) a second reservoir comprising an excess of fluoxetine salt at or below saturation when in equilibrium with the first reservoir;
   (c) a rate-controlling membrane between the first reservoir and the second reservoir;
   (d) a backing behind the body contacting-distal surface of the second reservoir; and
   (e) means for maintaining the first and second reservoirs in fluoxetine-transmitting relation with a body surface or membrane, said device having a surface area defining an area of fluoxetine delivery of less than about 60 cm$^2$, wherein a therapeutically effective amount of fluoxetine is delivered at a therapeutically effective rate within 250–3200 $\mu$g/hr during an administration period of at least 12 hours in order to provide therapeutic blood or plasma levels.

2. A device according to claim 1 wherein the salt is fluoxetine acetate or fluoxetine maleate.

3. A device according to claim 1 wherein the first reservoir further comprises an anti-irritant.

4. A device according to claim 3 wherein the anti-irritant comprises a corticosteroid in an amount effective to coadminister said corticosteroid at a rate in excess of 0.1 $\mu$g/cm$^2$·hr throughout the adminstration perid in order to reduce skin irritation wherein the total amount of corticosteroid delivered is less than 5 mg /24 hours.

5. A device according to claim 4 wherein the corticosteroid is hydrocortisone.

6. A device according to claim 3 wherein the first reservoir further comprises a permeation enhancing amount of a permeation enhancer.

7. A device according to claim 6 wherein the permeation enhancer comprise a monoglyceride or mixture of monoglyceride of a fatty acid.

8. A device according to claim 7 further comprising a cosolvent selected from the group consisting of fatty acid esters, lactate ester and alkyl laurates.

9. A device according to claim 8 wherein the monoglyceride is glycerol monolaurate and the cosolvent is selected from the group consisting of dodecyl acetate, lauryl lactate, and methyl laurate.

10. A device according to claim 6 wherein the first reservoir comprises 15 to 40 weight % fluoxetine acetate, 0.1 to 10 weight % hydrocortisone, and 10 to 40 weight % of a permeation enhancer comprising glycerol monolaurate and methyl laurate.

* * * * *